United States Patent [19]

Stewart

[11] Patent Number: 5,458,563
[45] Date of Patent: Oct. 17, 1995

[54] TOOTHBRUSHES

[76] Inventor: Timothy N. Stewart, 231 Derby Street, Sheffield, United Kingdom, S2 3NG

[21] Appl. No.: 50,280

[22] PCT Filed: Nov. 12, 1991

[86] PCT No.: PCT/GB91/01986

§ 371 Date: Jul. 2, 1993

§ 102(e) Date: Jul. 2, 1993

[87] PCT Pub. No.: WO92/08391

PCT Pub. Date: May 29, 1992

[30] Foreign Application Priority Data

Nov. 15, 1990 [GB] United Kingdom ............... 9024890

[51] Int. Cl.$^6$ .............................. A61H 9/00; A61F 5/00; A46B 13/00
[52] U.S. Cl. .................................. 601/162; 15/24; 15/29
[58] Field of Search ................................ 601/162, 163, 601/167; 433/80, 81, 91, 92, 93, 94, 95, 96, 216; 15/167.1, 167.2, 24, 29

[56] References Cited

U.S. PATENT DOCUMENTS

| 2,283,314 | 5/1942 | Ckola ................................. 15/24 |
| 2,285,865 | 6/1942 | Lowe et al. .......................... 15/24 |
| 2,303,667 | 12/1942 | Taborski ............................ 601/163 |
| 2,757,668 | 8/1956 | Meyer-Saladin ................. 601/162 X |
| 4,181,997 | 1/1980 | O'Rourke ............................ 15/24 |
| 4,672,953 | 6/1987 | DiVito ............................. 433/80 X |
| 5,062,413 | 11/1991 | Bullard ............................ 601/162 |

*Primary Examiner*—Nicholas D. Lucchesi
*Attorney, Agent, or Firm*—Trexler, Bushnell, Giangiorgi & Blackstone, Ltd.

[57] ABSTRACT

The invention relates to toothbrushes and particularly with toothbrushes for bedridden patients. Cleaning of the teeth of bedridden patients is particularly difficult and especially the rinsing of the mouth. It is an object of the present invention to provide a toothbrush that overcomes this difficulty, an objective that is met by a construction comprising a bristled head and a handle, there being a fluid supply associated with the handle and having an outlet emerging in the bristles on the toothbrush head, the fluid supply being connectable to a source of fluid, and there being a separate fluid disposal associated with the handle having an inlet associated with the bristles on the toothbrush head and to direct spent fluid away from the bristle head. In its most convenient form the invention comprises a transportable unit having a first container for fluid and a pump to drive fluid to the toothbrush and a second container with an associated vacuum pump for the extraction of fluid from within the mouth of the patient.

9 Claims, 1 Drawing Sheet

TOOTHBRUSHES

BACKGROUND OF THE INVENTION

This invention generally relates to toothbrushes. More particularly, this invention relates to toothbrushes and a portable oral hygiene system for bedridden users.

Conventionally, water is applied to the bristled head of a toothbrush to assist the cleansing action of a dentifrice applied to its bristles, and following brushing, there is the need to rinse the mouth. To the able bodied or to those able to sit upright without undue difficulty, cleaning the teeth is not particularly troublesome.

However, when it is the case of a bed-ridden patient, not able to sit upright, or only able to sit upright with considerable difficulty and discomfort, cleaning the teeth is particularly troublesome, and especially rinsing the mouth, as neither the application of water to assist the action of the dentifrice nor subsequent rinsing of the mouth can be effected in conventional manner with the patient in the prone position.

The object of the invention is to provide a toothbrush that overcomes those difficulties mentioned above.

SUMMARY OF THE INVENTION

According to the present invention, a toothbrush for selective connection to a source of fluid and to a spent fluid disposal means, is characterised by a handle portion, said handle portion including a first passageway extending through the handle portion from a bristled head portion at one end of the handle portion to the opposite end of the handle portion, said first passageway being connectable at the said opposite end of the handle portion to the source of fluid, said handle portion further including a second passageway disposed adjacent to the first passageway and extending through the handle portion from the bristled head portion to the said opposite end of the handle portion, said second passageway being connectable at said opposite end of the handle portion to the spent fluid disposal means, said handle portion still further including an air-bleed passage extending along the length of the handle portion and communicating at one end thereof with the bristled head portion, said air-bleed passageway communicating to atmosphere at a point remote from the bristled head portion.

A toothbrush selectively connectable to a source of fluid and to a spent fluid disposal means, the said toothbrush being characterised by a handle portion; and a bristled head portion disposed at one end of said handle portion, said handle portion including a first passageway extending through the handle portion from the bristled head portion to the opposite end of the handle portion, said first passageway having a cross-sectional area towards said bristled head portion smaller than the cross-sectional area of said first passageway towards said opposite end of said handle portion, said first passageway being connectable at the said opposite end of the handle portion to the source of fluid, said handle portion further including a second passageway disposed adjacent to the first passageway and extending through the handle portion from the bristled head portion to the said opposite end of the handle portion, said second passageway being connectable at the said opposite end of the handle portion to the spent fluid disposal means, and said handle portion further including an air-bleed passage extending along the length of the handle portion and communicating at one end thereof with the bristled head portion, said air-bleed passageway communicating to atmosphere at a point remote from the bristled head portion.

The connection of the fluid supply means to a source of fluid may simply be a hose attached to the conduit or to the handle portion that communicates with the first passageway, the hose extending to e.g. a conventional water tap. However, and particularly in hospitals, a patients bed may not be in reasonably close proximity to a water tap. Therefore, a self-contained fluid source may be provided, such as a relatively small container that can be placed in an elevated position with respect to the patient to gravity feed fluid to the toothbrush, or a relatively small container that includes a pump to pump fluid to the toothbrush. With either construction of the self-contained fluid source valve means may be provided, such as at the connection of the hose to the conduit or to the first passageway to serve as an ON/OFF valve for the supply of fluid for variable rate control for the fluid supply.

To enable the disposal of spent fluid, the second passageway formed in the handle portion may be connected to a hose in which is provided an appropriate suction pump, the outlet of the suction pump extending e.g. to a conventional sink. However, and as is the case with the fluid supply, a patient's bed may not be in reasonably close proximity to a sink and therefore a container can be placed proximate to a patient to gather spent fluid.

Preferably, the air-bleed passage extending from the base of the bristles to substantially the mid-point on the handle and where the communication to atmosphere is provided is therefore clear of the patient's mouth when in use, and whereby build-up of vacuum in a patient's mouth is prevented should the patient inadvertently close his/her mouth onto the toothbrush.

As a toothbrush must be dedicated to one user, the toothbrush of the present invention may be selectively disconnectable from the fluid source and the spent fluid disposal means. Thus, the toothbrush may be left with the patient when the hoses and containers are taken to a next patient. The toothbrush may alternatively have a detachable head that can be left with the patient with the handle portion permanently attached to the hoses.

In use, and following the application of dentifrice to the bristles, a small amount of fluid can be supplied to the bristles to moisten them, and after brushing the teeth, fluid allowed to flow to the bristles to enable the rinsing of the patients mouth. To dispose of surplus fluid, and particularly at the stage of rinsing of the patients mouth, the suction pump can be activated to draw fluid from the mouth and deposit it in the sink or the container for subsequent disposal.

To meet the requirements for a fluid source and spent fluid disposal means that can be placed near the patient, a convenient form of construction is to provide a relatively small, easily portable unit having a first container and supply pump to provide a supply of fluid and a second container and suction pump to remove fluid from a patient's mouth. Such a unit can be taken between patients provided there are conveniently located power sources available to provide power to the pumps. With this form of construction it would be possible to provide a third container containing an appropriate mouthwash, the third container having a pump and to supply a mouthwash to the patient's mouth after brushing and rinsing. It would be equally possible to maintain the unit with two containers and to use the mouthwash first to moisten the bristles at the point of application of dentifrice and to serve simultaneously to rinse the mouth and effect mouth washing.

One embodiment of the invention will now be described by way of example only, with reference to the accompanying drawings, in which:

FIG. 1 is a sectional side elevation of a toothbrush and handle in accordance with the invention; and FIG. 2 is a schematic partly-sectioned perspective view of a portable unit in accordance with the invention.

DESCRIPTION OF PREFERRED EMBODIMENT

Figure 1:
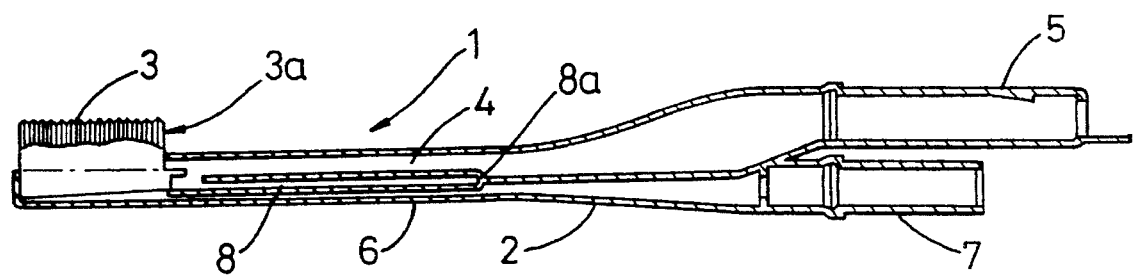

In FIG. 1, a toothbrush 1 constructed in accordance with the teachings of the present invention, comprises a handle portion 2 with a bristled head portion 3 disposed at one end of the handle portion 2. Within the handle portion 2 is a first passageway 4 extending from a first plug-like connector 5 at the opposite end of the handle portion 2 to the bristled head portion 3, and a second passageway 6 extending from a second plug-like connector 7 also at the opposite end of the handle portion 2 to the bristled head portion 3, an outlet (not shown) from the first passageway 4 and an inlet (not shown) to the second passageway 6 communicating with the bristles 3a of the bristle head portion 3. Also in communication with the bristled head portion 3 is an air-bleed passage 8 extending along the handle portion 2 from the head portion 3 to a passageway 8a formed in the wall of the handle portion 2 and communicating the air-bleed passageway to atmosphere. The passageway 8a is disposed substantially at a mid-portion of the handle portion 2. As can be seen in FIG. 1, first passageway 4 is preferably formed having a cross-sectional area that is smaller towards the bristled head portion than it is towards the opposite end of the handle portion 2 to the first end of the handle portion 2. In a similar manner, second passageway 6 is smaller in cross-section towards the bristled head portion than towards the opposite end of the handle portion 2.

Figure 2:
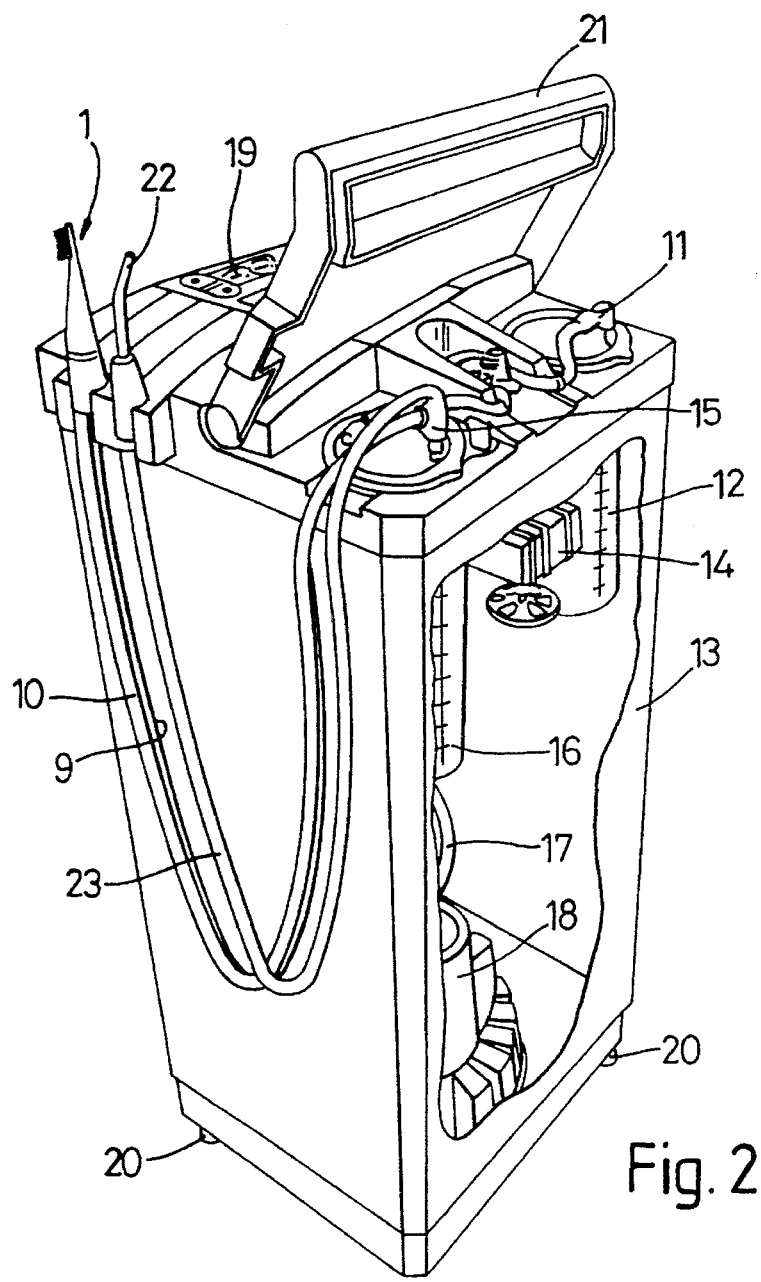

As is shown by FIG. 2, the plug-like connectors 5 and 7 are connected respectively to first and second hoses 9 and 10, the first hose 9 extending to a first connection 11 to a fluid supply container 12 disposed within a portable housing 13. Associated with the first hose 9 is a peristaltic pump 14 for the supply of fluid from the fluid supply container 12 and along the first hose 9, from where the fluid passes along the passageway 4 to emerge in the bristles of the bristle head portion 3. The peristaltic pump 14 preferably has a variable speed drive. Thus, and with dentifrice applied to the bristles 3a of the bristle head portion 3, a small quantity of fluid can be supplied to the bristle head portion 3, to moisten the bristles 3a and assist with the cleansing action of the dentifrice. Following cleaning of the teeth and to enable effective rinsing of a patient's mouth, the pump 14 may be driven at a greater rate to supply a greater volume of fluid to the patient's mouth and to enable effective rinsing. The second hose 10 extends to a second connection 15 and to a fluid collector 16, the second hose 10 being further connected by an air line 17 to a vacuum pump 18 located within the portable housing 13. Thus, and particularly at the point of rinsing of a patient's mouth, the vacuum pump 18 can be switched on to create a vacuum in the second hose 10 and hence in the second passageway 6 in the toothbrush handle to cause the extraction of fluid from within the patient's mouth through the bristle head portion 3 and to cause deposit of the spent fluid in the fluid collector 16. It will be understood that a vacuum may be applied at the bristle head portion 3 when spent fluid is removed therefrom by action of the vacuum pump 18. Thus, if a patient closes his or her mouth around the bristled head portion 3 in such an event, a vacuum may be applied to the closed mouth of the patient. This is undesirable. The air bleed passage 8 prevents the build-up of a vacuum in a patient's mouth. Should the patient's mouth inadvertently close around the bristled head portion 3 of the toothbrush 1 during operation of the vacuum pump 18, air is drawn through the passageway 8a communicating to atmosphere into the air bleed passage 8 and into the bristled head portion 3 to prevent an unacceptable build-up of vacuum in the patient's mouth. Air-bleed passage 8 communicates with the bristled head portion 3 via first passageway 4 as illustrated in FIG. 1.

Conveniently located at the top of housing 13 is a control panel 19 suitably connected to the motor of the peristaltic pump 14 and the motor of the vacuum pump 18 to enable either or both motors to be switched on and off and to cause the motor, particularly the motor of the peristaltic pump 14, to be as and when required.

To enable the easy transport of the unit from patient to patient, the housing 13 is preferably provided with wheels means 20 at its base, and a handle 21 at its upper end.

Whilst the construction as is described above is highly effective for patients who, whilst they must remain prone, are conscious, there are particular difficulties attendant to patients in an unconscious or semi-conscious condition. Therefore, and particularly for use with such unconscious and semi-conscious patients, it is preferred to provide additional fluid extraction means. Thus, a fluid extractor 22 may be provided connected by a hose 23 to the second connection 15 and thereby to the fluid collector 16. Further, preferably, said fluid extractor 22 is selectively connectable to the vacuum pump 18 and operable by an appropriate switch on the control panel 19, when required.

I claim:

1. A toothbrush selectively connectable to a source of fluid and to a spent fluid disposal means, said toothbrush comprising a handle portion, said handle portion including a first passageway extending through the handle portion from a bristled head portion at one end of the handle portion to an opposite end of the handle portion, said first passageway being connectable at the said opposite end of the handle portion to the source of fluid, said handle portion further including a second passageway disposed adjacent to the first passageway and extending through the handle portion from the bristled head portion to the said opposite end of the handle portion, said second passageway being connectable at said opposite end of the handle portion to the spent fluid disposal means, said handle portion further including an air-bleed passageway extending along the length of the handle portion and communicating at one end thereof with the bristled head portion, said air-bleed passageway communicating to atmosphere at a point remote from the bristled head portion.

2. A toothbrush as in claim 1, wherein the bristled head portion is selectively detachable from the handle portion.

3. A toothbrush as in claim 1, wherein the bristled head portion is permanently affixed to the handle portion.

4. A toothbrush as in claim 1, further comprising a transportable, self-contained unit including first container means for the source of fluid and second container means for the spent fluid.

5. A toothbrush as in claim 4, wherein said first container means is selectively removable from the transportable unit, and said second container means is selectively removable from the transportable unit.

6. A toothbrush selectively connectable to a source of fluid and to a spent fluid disposal means, the said toothbrush comprising a handle portion; and a bristled head portion disposed at one end of said handle portion, said handle portion including a first passageway extending through the handle portion from the bristled head portion to the opposite end of the handle portion, said first passageway having a cross-sectional area towards said bristled head portion smaller than the cross-sectional area of said first passageway towards said opposite end of said handle portion, said first passageway being connectable at the said opposite end of the handle portion to the source of fluid, said handle portion further including a second passageway disposed adjacent to the first passageway and extending through the handle portion from the bristled head portion to the said opposite end of the handle portion, said second passageway being connectable at the said opposite end of the handle portion to the spent fluid disposal means, and said handle portion further including an air-bleed passageway extending along the length of the handle portion and communicating at one end thereof with the bristled head portion, said air-bleed passageway communicating to atmosphere at a point remote from the bristled head portion.

7. A toothbrush as in claim 6, wherein said second passageway is formed having a cross-sectional area towards the bristled head portion smaller than the cross-sectional area towards the said opposite end of the handle portion.

8. A toothbrush as in claim 6, wherein said communication of said air-bleed passageway to atmosphere is disposed substantially at a mid-portion of the handle portion.

9. A toothbrush as in claim 6, wherein said air-bleed passageway communicates with the bristled head portion via the first passageway of the handle portion.

\* \* \* \* \*